(12) United States Patent
Sherman et al.

(10) Patent No.: US 6,854,322 B2
(45) Date of Patent: Feb. 15, 2005

(54) DIRECTIONAL COUPLER SENSOR

(75) Inventors: Faiz Feisal Sherman, West Chester, OH (US); Vladimir Gartstein, Cincinnati, OH (US); Kendal William Kerr, Okeana, OH (US); Herman William Meyer, Cincinnati, OH (US); Jim Allen McCurdy, Liberty Township, OH (US)

(73) Assignee: The procter & Gamble Company, Cincinnati, OH (US)

( * ) Notice: Subject to any disclaimer, the term of this patent is extended or adjusted under 35 U.S.C. 154(b) by 3 days.

(21) Appl. No.: 10/442,503

(22) Filed: May 21, 2003

(65) Prior Publication Data

US 2003/0226397 A1 Dec. 11, 2003

Related U.S. Application Data (60) Provisional application No. 60/387,474, filed on Jun. 10, 2002.

(51) Int. Cl.⁷ .......................... G01N 25/56; G01R 27/08
(52) U.S. Cl. ............................. 73/73; 324/693; 324/694
(58) Field of Search ................................ 324/692, 693, 324/694; 73/73, 29.01, 335.02, 335.04, 335.03, 335.05

(56) References Cited

U.S. PATENT DOCUMENTS

| | | | | |
|---|---|---|---|---|
| 3,755,733 A | * | 8/1973 | Vankoughnett et al. ...... | 324/640 |
| 4,358,731 A | * | 11/1982 | Steinbrecher ................ | 324/636 |
| 4,364,008 A | * | 12/1982 | Jacques ........................ | 324/636 |
| 4,378,168 A | * | 3/1983 | Kuisma et al. ................ | 374/28 |
| 5,256,978 A | * | 10/1993 | Rose ............................ | 324/601 |
| 5,315,258 A | * | 5/1994 | Jakkula et al. .............. | 324/640 |
| 5,767,685 A | * | 6/1998 | Walker ........................ | 324/640 |
| 6,237,417 B1 | * | 5/2001 | Lonsdale et al. ............. | 73/579 |

FOREIGN PATENT DOCUMENTS

| | | | |
|---|---|---|---|
| DE | 3938391 A1 | * | 7/1990 |
| JP | 57-163860 A | | 10/1982 |
| SU | 1453275 A | * | 1/1989 |
| WO | WO-98/21818 | * | 5/1998 |

OTHER PUBLICATIONS

Abrosimova, E.B., et al., "Amplitude UHF Humidity Meter For Solid And Powdered Materials," *Measurement Techniques*, vol. 39, No. 11, Nov. 1, 1996, pp. 1162–1165.

Nagata, H., "Hair Moisture Meter HC–1000," *Sharp Technical Journal*, 1985, Japan, No. 33, pp. 151–152.

Kupfer, K., et al., "Materialfeuchtemessung mit Mikrowellen (Moisture measurement with microwaves)", *Technisches Messen TM*, R. Oldenbourg Verlag, Munchen, Germany, vol. 59, No. 3, Mar. 1, 1992, pp. 110–115.

* cited by examiner

*Primary Examiner*—Michael Cygan
(74) *Attorney, Agent, or Firm*—Bart S. Hereko; Larry L. Huston; Brian M. Bolam (57) ABSTRACT

A directional coupler sensor is provided for measuring the moisture content of a substrate, such as hair. The sensor incorporates a high frequency directional coupler having a pair of generally parallel plates defining a coupling gap therebetween. A high frequency signal generator generates an electromagnetic field across the gap with the substrate placed across the coupling gap. The coupled power relates to the moisture content of the substrate. A pressure sensor is provided to ensure that the desired compactness of the substrate across the coupling gap is achieved to obtain accurate, reliable and consistent results.

8 Claims, 9 Drawing Sheets

DIRECTIONAL COUPLER SENSOR

CROSS REFERENCE TO RELATED APPLICATIONS

This application claims the benefit of U.S. Provisional Application No. 60/387,474, filed Jun. 10, 2002.

FIELD OF THE INVENTION

The present invention relates generally to measurement sensors and, more particularly, to a sensor for measuring a property of a substrate, such as the internal and external moisture content of biological systems such as hair.

BACKGROUND OF THE INVENTION

Human hair is made up of a complex protein called alpha-keratin. Protein molecules of the hair are arranged in organized patterns and are held together by weak bonds, such as hydrogen, saline and hydrophobic bonds, and stronger ionic bonds and sulphur bridges. These bonds lend stiffness or rigidity to the hair and enable styling of the hair with waves and curls as these bonds are broken and then re-established in different orientations through the styling process. As is known, styling of hair may be accomplished by breaking the bonds by adding energy to the hair, such as by heat with a curling iron or blow dryer, or by getting the hair wet or damp. When the hair is wet or damp and the hydrogen bonds are broken, the hair becomes elastic and can be stretched and given a particular form since the position of the keratin chains has been altered. As the hair dries, the bonds reform in different places, maintaining the hair in its new shape. Blow-drying or setting assists in controlling the styling process so that, once dry, the hair will retain the form it has been given.

Hair is hydroscopic and permeable so it will absorb water from the environment. Under normal conditions, water accounts for about 12% to 15% of the composition of hair. Normal hair can absorb more than 30% of its own weight in water. If the hair is damaged, this percentage can approach 45%, however damaged hair has less ability to retain water within the hair fibers which gives hair its healthy appearance. As more water is absorbed within the hair fiber due to humidity or prior damage, the hydrogen bonds may loosen so that the hair has a decreased ability to maintain its set.

During styling, if the hair is too wet, it will not hold its shape and water must be removed before styling will be effective. Conversely, when the hair is too dry, the hydrogen bonds will have already been formed and poor styling will result since the keratin chains cannot be repositioned and set. It has previously been determined that optimum styling results may be achieved when the moisture of hair is in the range of approximately 30–40% by weight. It is thus desirable to be able to tell when to begin styling (i.e., when moisture in the hair is in a range of 30–40%) to obtain the optimum styling results.

Likewise, it is also important to know when to stop styling hair which has been wetted to break the hydrogen bonds. If the hair is too dry, it will not be flexible and potential damage of the hair may result when styling is continued. It has been determined that the process of drying hair exhibits two stages which are relevant to styling. In a primary drying stage, water is evaporated from the outside of the hair fibers and no styling benefit is achieved. In a secondary drying stage, water from inside the hair fibers is diffused to the environment. It is during this transition to the secondary drying stage when optimum styling of hair may be achieved. A moisture level of about 30% is a balance between providing enough water to disrupt the hydrogen bonds to allow the hair to shape and not enough water that must be removed for the hydrogen bonds to be reformed.

Moisture sensing devices have been developed in the past to determine the moisture level in hair, and have relied on various techniques including resistance and capacitance measurements to obtain the desired indication. However, these methods only work well for a known cross sectional quantity and density of the hair being measured. As the hair density or compactness is varied, these measurement techniques fail. Additionally, these techniques rely primarily on the moisture content outside of the hair fiber for the measurement, and do not have the ability to accurately measure moisture content within hair fibers as well.

Thus, there is a need for a sensing device which can accurately and reliably determine the moisture content of a substrate, such as hair, including moisture both inside and outside of the hair fiber.

SUMMARY OF THE INVENTION

The present invention overcomes the foregoing and other shortcomings and drawbacks of moisture sensors and methods of determining moisture content heretofore known. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention a directional coupler sensor is provided for measuring the moisture content of a substrate, such as hair. As the moisture content of a substrate increases, so does its effective relative electrical impedance. The sensor of the present invention is designed to measure the relative impedance of a substrate, and from that measurement, the moisture content of the substrate can be determined.

The sensor of the present invention incorporates a high frequency directional coupler having a pair of generally parallel strips that define a coupling gap therebetween. A high frequency signal generator is electrically coupled to one of the strips and generates an electromagnetic field across the coupling gap to couple power to the other strip with the substrate placed across, i.e., generally normal to the longitudinal axis of, the coupling gap. The signal generator is preferably operable to generate signals in the VHF to UHF frequency ranges, although other frequency ranges are possible as well. The VHF frequency range is between about 30 MHz and 300 MHz, and the UHF frequency range is between about 300 MHz and about 3 GHz. The signal generator generates a coupled power signal in the coupled strip that has an amplitude related to the impedance, and therefore the moisture content of the substrate placed across the coupling gap.

In accordance with another aspect of the present invention, a pressure sensor is provided to ensure a proper packing pressure of the substrate placed across the coupling gap. The pressure sensor incorporates a film transducer in one embodiment that generates an output voltage signal that varies with the packing pressure applied to the substrate placed across the coupling gap. The measurement of the moisture content of the substrate is triggered upon the crossing of a pre-set pressure threshold. This ensures that the desired compactness of the substrate placed across the coupling gap is achieved to obtain accurate, reliable and consistent results. Alternatively, the packing consistency can be achieved by a mechanical system as well. The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION OF THE PREFERRED EMBODIMENT

Referring now to the Figures, and to FIGS. 1 and 2A–2E in particular, a directional coupler sensor 10 is shown in accordance with the principles of the present invention. For the sake of simplicity, the sensor 10 will be described herein in connection with measuring the moisture content of hair. However, it will be appreciated by those of ordinary skill in the art that the present invention has use in a wide variety of applications and is therefore not limited to the analysis of hair or the measurement of moisture content in a substrate. Rather, the sensor 10 of the present invention is readily adaptable to analyze a wide variety of substrates and to measure different moisture related properties of those substrates as will be readily appreciated by those of ordinary skill in the art.

For example, in the measurement of the moisture content of a substrate, the sensor 10 of the present invention operates under the principle that as the moisture content of a substrate increases, so does its effective relative electrical impedance. As will be described in greater detail below, the sensor 10 is designed to measure the relative impedance of a substrate, and from that measurement, the moisture content of the substrate can be determined. The moisture content value may be presented on a visual display, indicated through a user-perceptible audible tone and/or used as a control signal to control a function of a device.

As shown in FIGS. 1, 2A–2E, 3 and 3A, the sensor 10 incorporates a high frequency directional coupler 12 having a pair of generally parallel strips 14a and 14b that define a coupling gap 16 therebetween. In one embodiment of the present invention, the parallel strips 14a, 14b are supported on an FR4 printed circuit board 18 (FIGS. 3 and 3A) having a ground plane 20 formed on a lower surface of the board 18. In one embodiment of the present invention, the height "h" of the PCB 18 is 0.062 in., each strip 14a, 14b has a width "w" of 0.15 in. and a length "l" of 0.350 in., and the coupling gap 16 has a gap distance "s" of 0.020 in. Of course, it will be appreciated by those of ordinary skill in the art that other dimensions of the PCB 18, strips 14a, 14b and gap 16 are possible as well depending on a particular application as will be described in detail below.

A high frequency signal generator 22 is electrically coupled to strip 14a and is operable to generate an electromagnetic field across the coupling gap 16 that couples power to strip 14b with the substrate placed across, i.e., generally normal to the longitudinal axis of, the coupling gap 16 in a packed manner as will be described in detail below. The signal generator 22 generates a coupled power signal in the coupled strip 14b that has an amplitude related to the impedance, and therefore the moisture content, of the substrate placed across the coupling gap 16. The signal generator 22 is phase locked to a crystal reference 24 (FIG. 2A) to maintain frequency and therefore measurement accuracy, stability and repeatability and has an adjustable power 26. The signal generator 22 is preferably operable to generate signals in the VHF to UHF frequency ranges, i.e., between about 30 MHz and about 3 GHz, although other frequency ranges are possible as well. In accordance with one embodiment of the present invention, the signal generator 22 may operate at about 1 GHz, such as at about 915 MHz, since it is contemplated that the water content of a substrate may be most accurately determined by its measured impedance in the near GHz range.

In accordance with one aspect of the present invention, the sensor 10 utilizes the reverse power coupling variation of the high frequency directional coupler 12 to measure the change in the impedance of the material placed across the coupling gap 16. As the substrate is packed across the coupling gap 16, the directional coupler 12 becomes mismatched, and this mismatch causes a monotonic increase in the reverse power coupling of the directional coupler 12 as the impedance across the gap 16 is increased as the result of increased moisture content of the material. The amplitude of the reversed power in the reflected power leg 28 (FIGS. 1 and 2B) from strip 14b is generally a direct measure of the impedance, and hence the moisture content, of the substrate placed across the coupling gap 16. As will be described in detail below, the moisture content of the substrate, i.e., its water content by weight, can be determined from the measured impedance of the sample.

Further referring to FIGS. 1 and 2A–2E, the forward power signal from strip 14a is electrically coupled to one port of a mixer 30 through a forward power leg 32 (FIGS. 1 and 2B) and an attenuator 34. For example, the forward power signal may be attenuated to about −10 dBm by the attenuator 34. The coupled power signal from strip 14b is phase shifted by phase shifter 36 and is electrically coupled to another port of the mixer 30 through the reflected power leg 28. The mixer 30 may act as a coherent receiver in that it is most responsive to coupled signals that are in phase with the forward power signal. The phase shifter 36 assures the proper phase coherence of the reflected power signal relative to the forward power signal for the mixer 30 to produce the maximum discernable mixer output. With the mixer forward power set to the appropriate level through the adjustable power 26, the output of the mixer 30 monotonically increases with an increase in the reflected coupled power. The mixer 30 demodulates or reduces to DC base band the value of the coupled power though the directional coupler 12. The DC output of the mixer 30 is filtered and amplified by amplifier 38 to produce a measurable output voltage that is related to the moisture content of the substrate placed across the gap 16. The amplifier 38 includes an adjustable gain 40 and an adjustable DC offset 42.

Figures 3, 3A, 4:
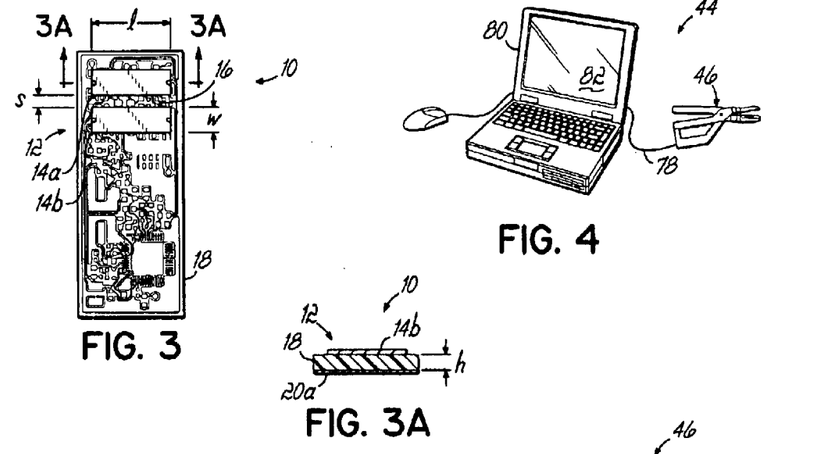
FIG. 3 is a top plan view of the sensor of FIG. 1 shown integrated onto a printed circuit board.
FIG. 3A is a cross-sectional view taken along line 3A—3A of FIG. 3.
FIG. 4 is a perspective view of a directional coupler sensor system in accordance with one embodiment of the present invention.
Figure 4A:
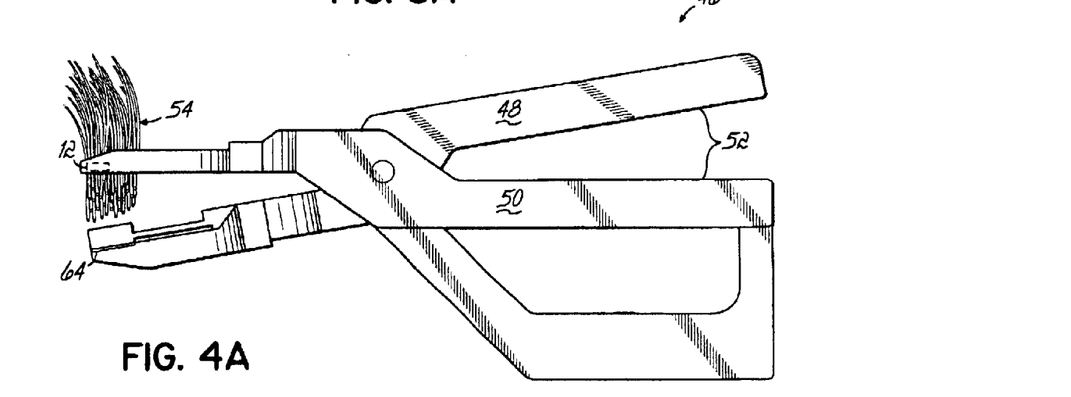
FIG. 4A is an enlarged front elevational view of a hair clamping device for use in the sensor system of FIG. 4, illustrating the clamping device in an open position to receive hair in the device.
Figure 4B:
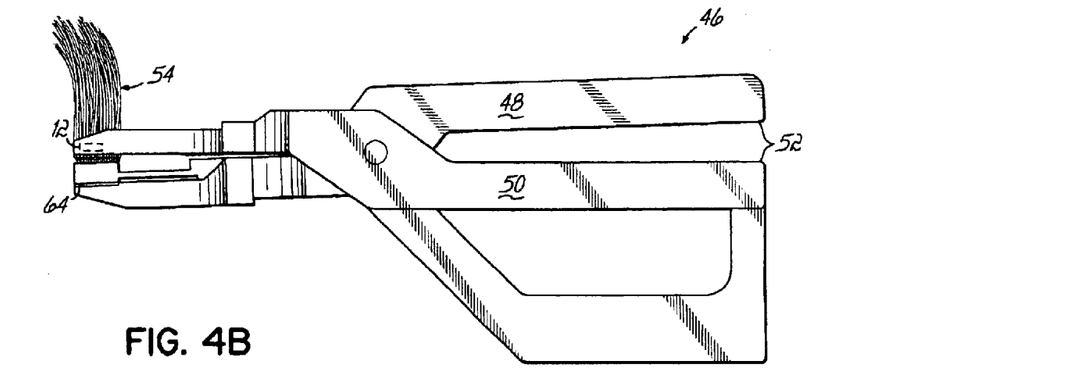
FIG. 4B is a view similar to FIG. 4A, illustrating the clamping device in a closed position to clamp hair in the device.

Referring now to FIGS. 4, 4A and 4B, use of the sensor 10 to determine the moisture content of hair will now be described in connection with a hair moisture sensor system 44. Hair moisture sensor system 44 may be used by a professional salon, for example, to quickly, accurately and reliably indicate to a stylist when the moisture content of a customer's hair is in the range of approximately 30–40% by weight so that the optimum styling results may then be achieved.

Figure 8:
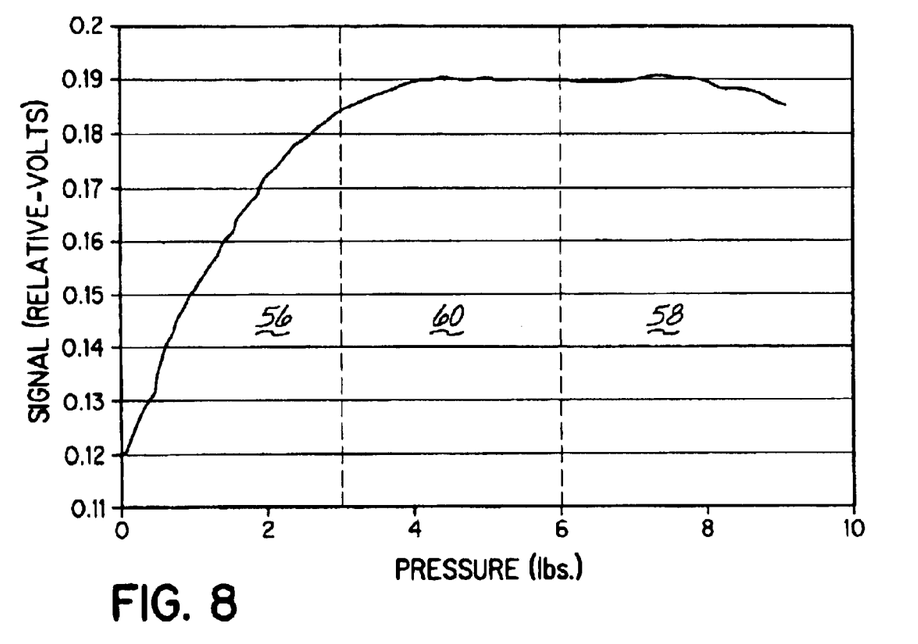
FIG. 8 is a graph illustrating the relationship between output voltage of the directional coupler sensor and pressure applied to pack the hair.

As shown in FIGS. 4A and 4B, a hair clamping device 46 is provided having pivoted jaws 48 and 50 that each terminate in a handle 52 that may be easily grasped and manipulated by the stylist. The jaws 48 and 50 may be biased to an open position as shown in FIG. 4A so that a bundle of hair 54 is readily received between the jaws 48, 50 and is oriented with the hair fibers 54 extending across, i.e., generally normal to the longitudinal axis of, the coupling gap 16 of the directional coupler 12 which is supported by jaw 50. As shown in FIG. 8, it has been determined that the packing pressure of the hair 54 across the coupling gap 16 is important to ensure reliability in the moisture content measurement. With low packing density below about three (3) lbs., i.e., a packing density in the pressure region 56, the output voltage signal of the mixer 30 may be unstable due to insufficient packing density of the hair fibers 54 across the coupling gap 16. At higher packing pressures above about seven (7) lbs., i.e., a packing density in the pressure region 58, the output voltage signal of the mixer 30 begins to fluctuate as the hair fibers 54 will exhibit the result of difference in packing density across the coupling gap 16. At these higher pressures, excess moisture is also quickly expelled resulting in unreliable lower readings. It has been determined that packing pressures in the range of about three (3) lbs. to about six (6) lbs., i.e., a packing pressure in the pressure region 60, provides an output voltage signal from the mixer 30 that is stable to produce reliable and repeatable measurements of the moisture content.

Figure 1:
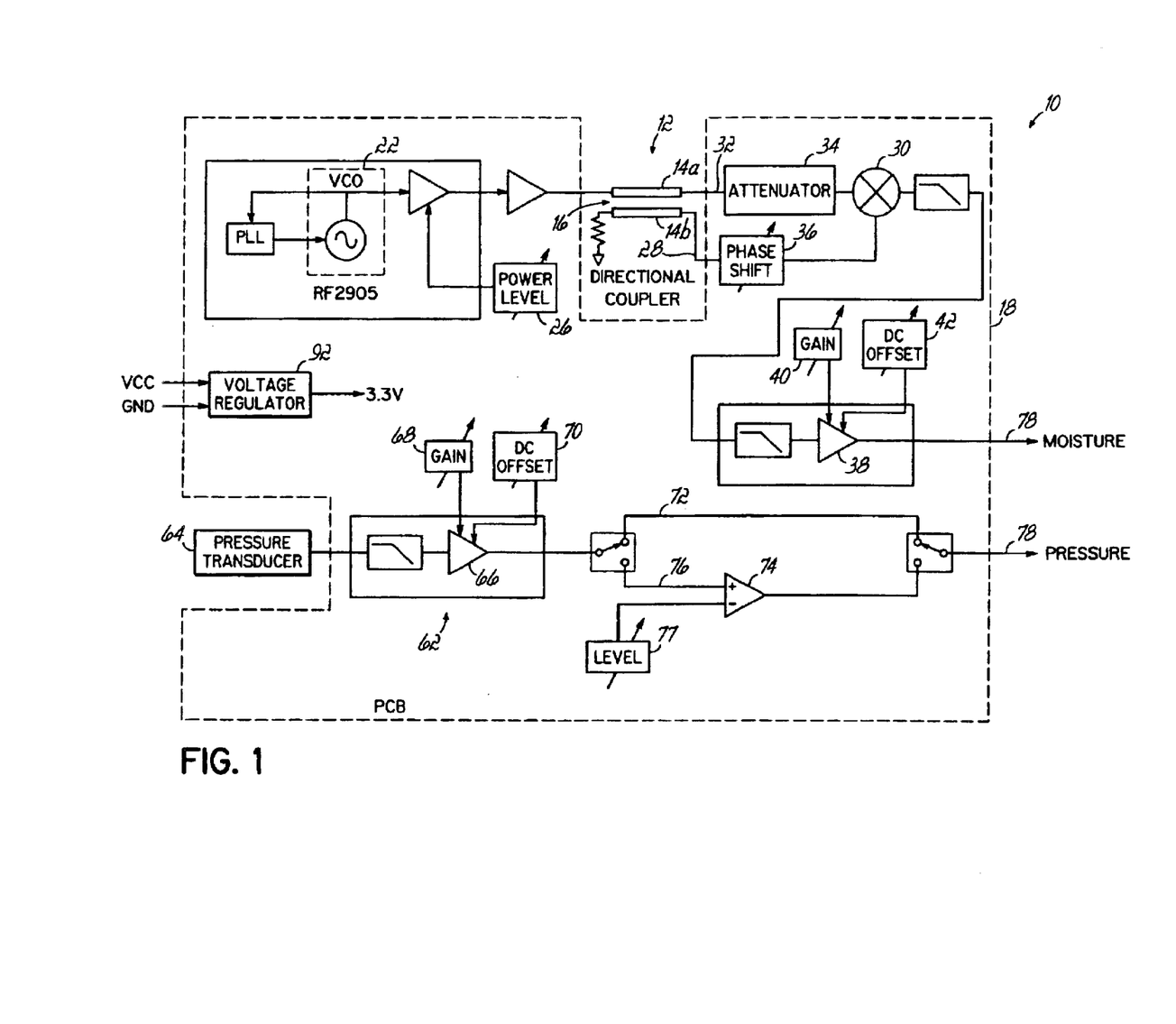
FIG. 1 is a functional block diagram of a directional coupler sensor in accordance with the principles of the present invention.
Figure 2A:
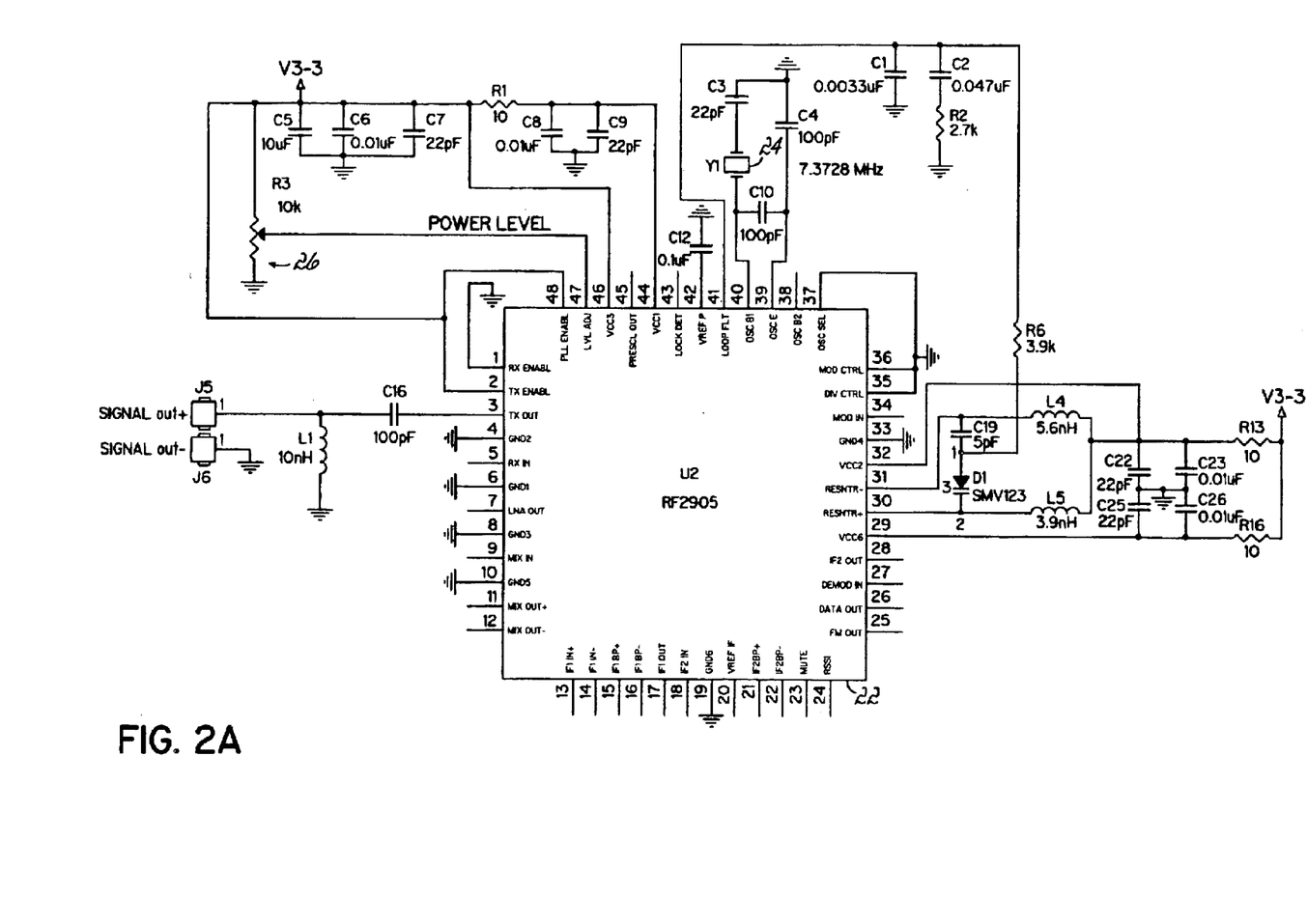
FIG. 2A is a circuit representation of a high frequency signal generator for use in the sensor of FIG. 1 in accordance with one embodiment of the present invention.
Figure 2B:
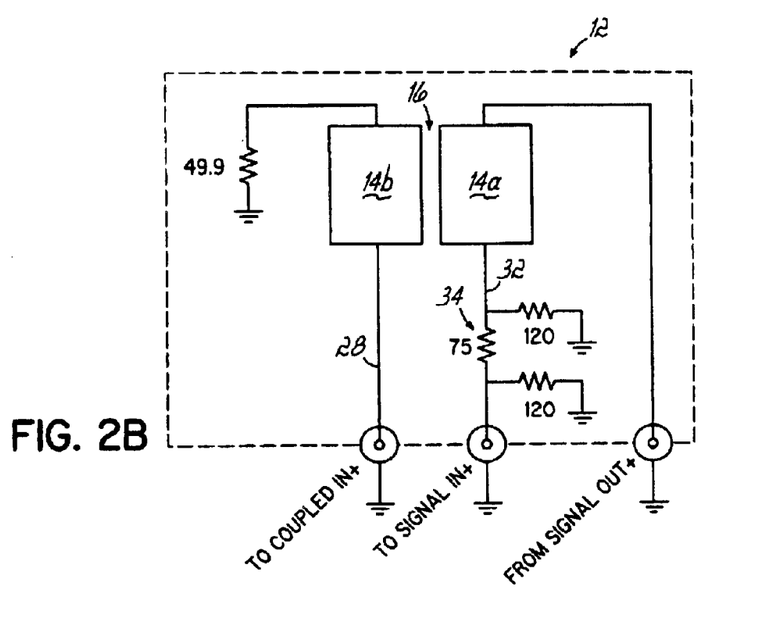
FIG. 2B is a circuit representation of a directional coupler for use in the sensor of FIG. 1 in accordance with one embodiment of the present invention.
Figure 2C:
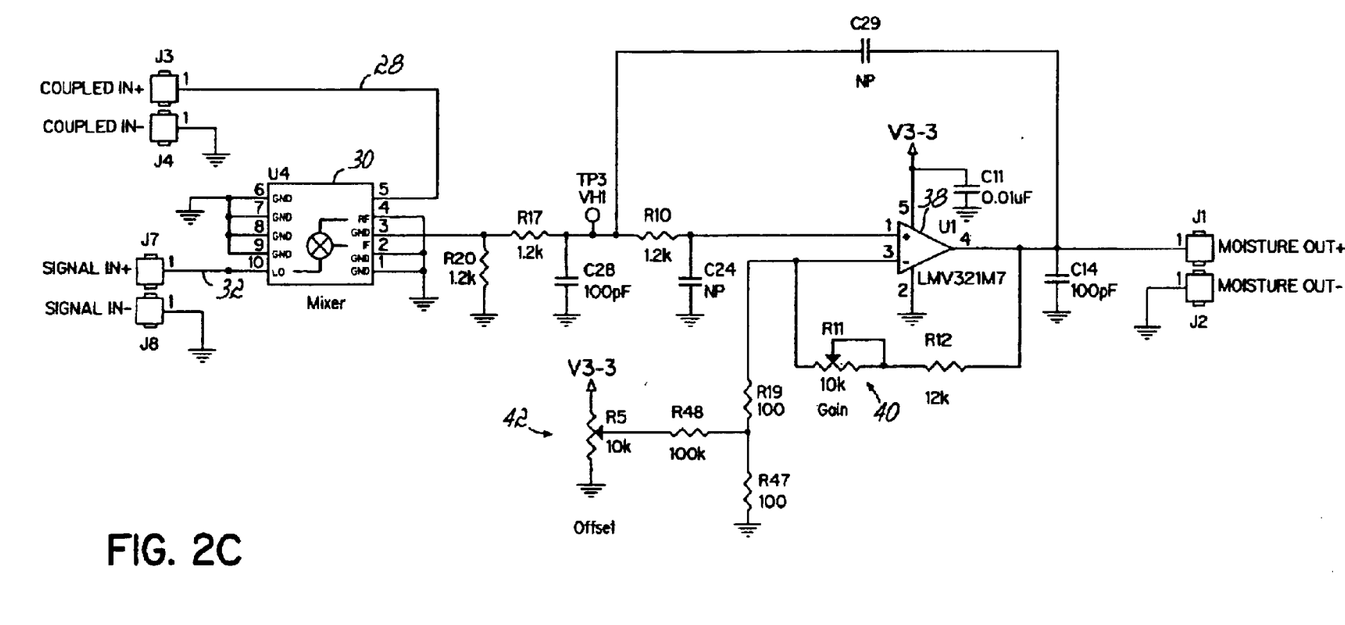
FIG. 2C is a circuit representation of a moisture content detector for use in the sensor of FIG. 1 in accordance with one embodiment of the present invention.
Figure 2D:
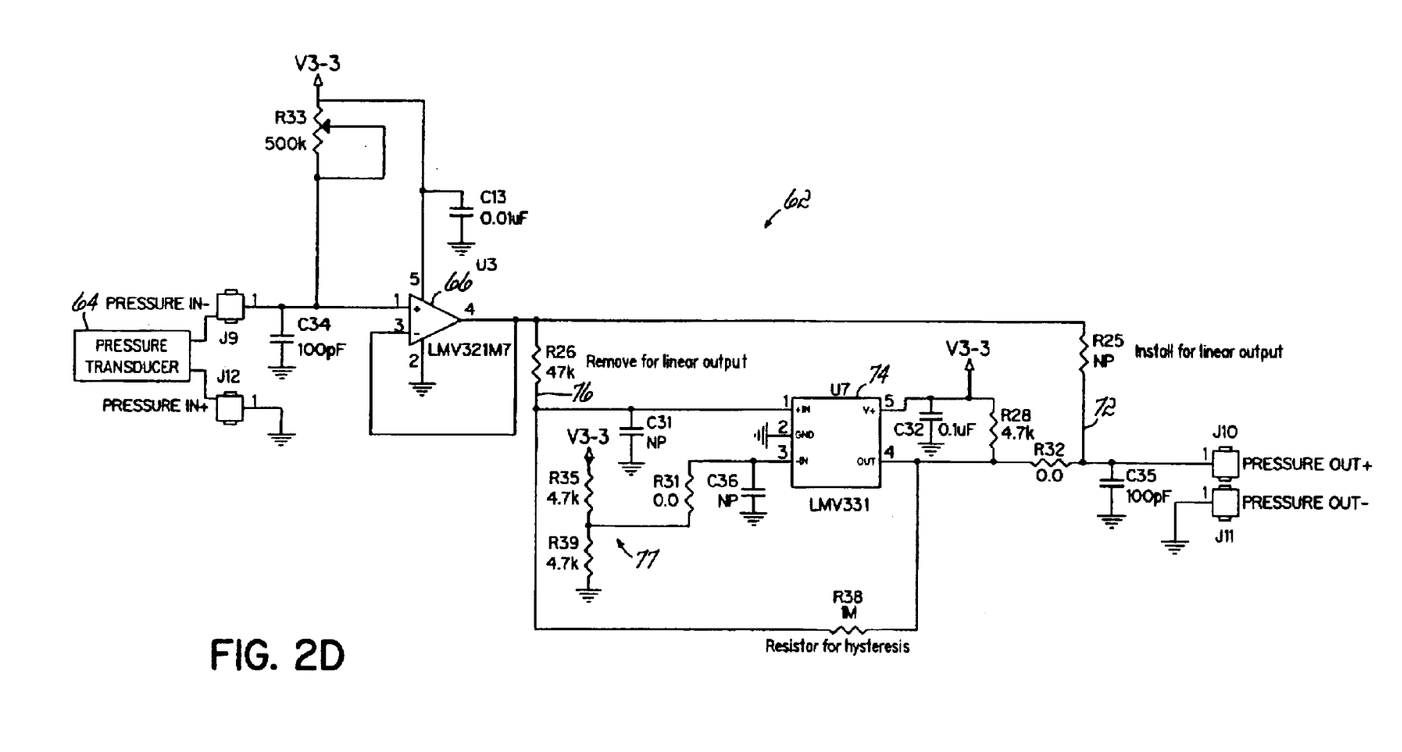
FIG. 2D is a circuit representation of a pressure sensor for use in the sensor of FIG. 1 in accordance with one embodiment of the present invention.
Figure 2E:
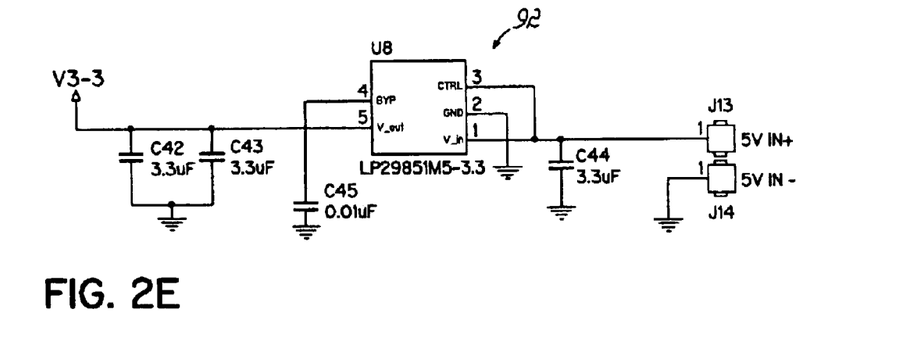
FIG. 2E is a circuit representation of a voltage regulator for use in the sensor of FIG. 1 in accordance with one embodiment of the present invention.

In accordance with another aspect of the present invention, as shown in FIGS. 1, 2D, 4A and 4B, a pressure sensor 62 incorporating a film pressure transducer 64, is supported by the jaw 48 in juxtaposition to the directional coupler sensor 12. The pressure transducer 64 is operable to generate an output voltage signal that varies with the packing pressure applied to the hair 54 placed across the coupling gap 16. As shown in FIGS. 1 and 2D, the output voltage signal from the pressure transducer 64 is amplified by amplifier 66 having an adjustable gain 68 and DC offset 70, and that amplified output voltage signal is either provided directly at the output of the pressure sensor 62 through jumper 72, or it is applied as an input to a comparator 74 through jumper 76. A trigger voltage corresponding to a desired trigger pressure is set as a reference voltage 77 to the comparator 74. The measurement of the moisture content is triggered upon the crossing of the pre-set pressure threshold 77. This ensures that the desired compactness of the hair fibers 54 placed across the coupling gap 16 is achieved to obtain accurate, reliable and repeatable results. It will be understood by those of ordinary skill in the art that packing consistency can be achieved by a mechanical system (not shown) as well without departing from the spirit and scope of the present invention.

With reference to FIGS. 1 and 4, the measured signal from the sensor 10, and the trigger signal or pressure signal from the pressure sensor 62, are electrically coupled through a cable 78 to a processing system 80, such as a conventional PC or laptop computer. The processing system 80 is operable to convert the measurement signal generated by the sensor 10 into a moisture content value that may be presented on the display 82 of the system 80. As described in detail above, the measurement signal is triggered in response to the trigger signal generated by the pressure sensor 62. One or multiple measurements signals may be taken in response to the trigger signal.

Figure 6:
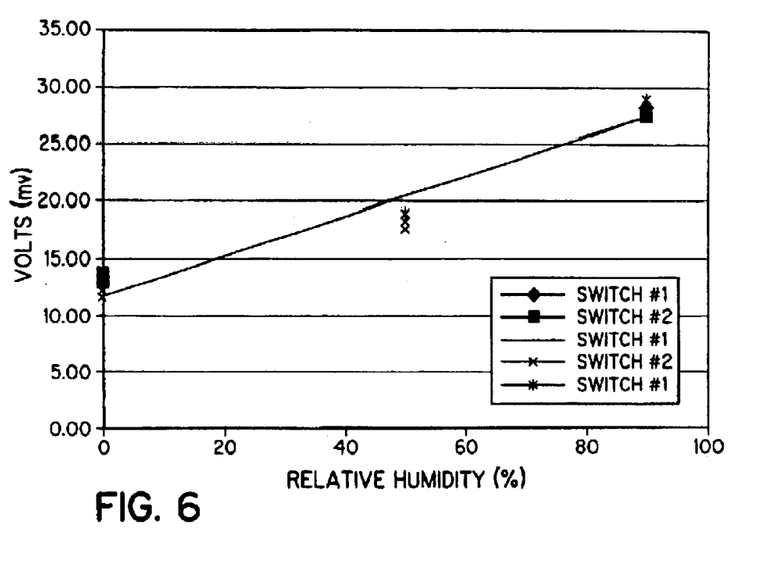
FIG. 6 is a graph illustrating the relationship between output voltage of the directional coupler sensor and relative humidity for various switches of hair.
Figure 7:
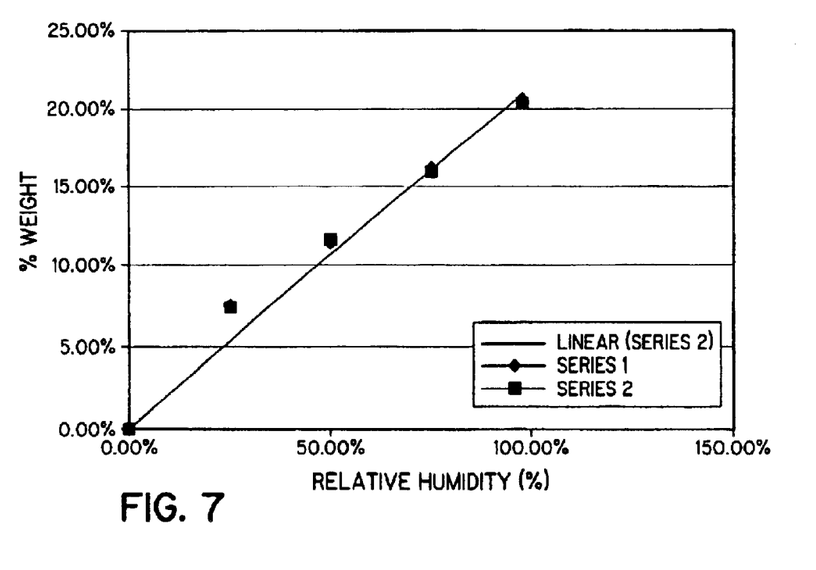
FIG. 7 is a graph illustrating the relationship between moisture content of hair by weight and relative humidity of hair.

Referring now to FIGS. 6 and 7, the amplified output voltage of the sensor 10 is calibrated by first subjecting multiple switches of hair to a known moisture content via the use of relative humidity. The sensor 10 is then used to generate a measurement signal for each switch of hair at the various relative humidities, as shown in FIG. 6. Since hair exhibits a generally linear relationship between moisture content by weight and relative humidity as shown in FIG. 7, the processing system 80 is operable to convert the amplified output voltage of the sensor 10 into a value representing the moisture content by weight of the hair using a look-up table or algorithm. Since the water absorption capability of damaged hair and healthy hair will differ, the sensor 10 of the present invention may be used to provide a signal that is generally related to the health of the hair. Generally, the health of hair is characterized by such factors as smoothness, shine, absence of frigility, absence of fissuring and absence of cuticular breakdown. As each of these factors is directly or indirectly related to the moisture content of the hair, the sensor 10 of the present invention is able to provide an accurate and reliable indication of the health of measured in vivo or in vitro hair.

The sensor 10 of the present invention provides a consumer friendly self-assessment tool that permits a consumer to periodically measure the general health of the consumer's hair. Based on these measurements, the consumer is able to take corrective actions as necessary which tend to improve the health of the consumer's hair. These actions may include changing hair care products, changing hair styling techniques, or both, so that the general health of the consumer's hair can be consistently monitored and improved. The sensor 10 also provides a useful monitoring tool to hair stylists and hair technicians as well.

Figure 5A:
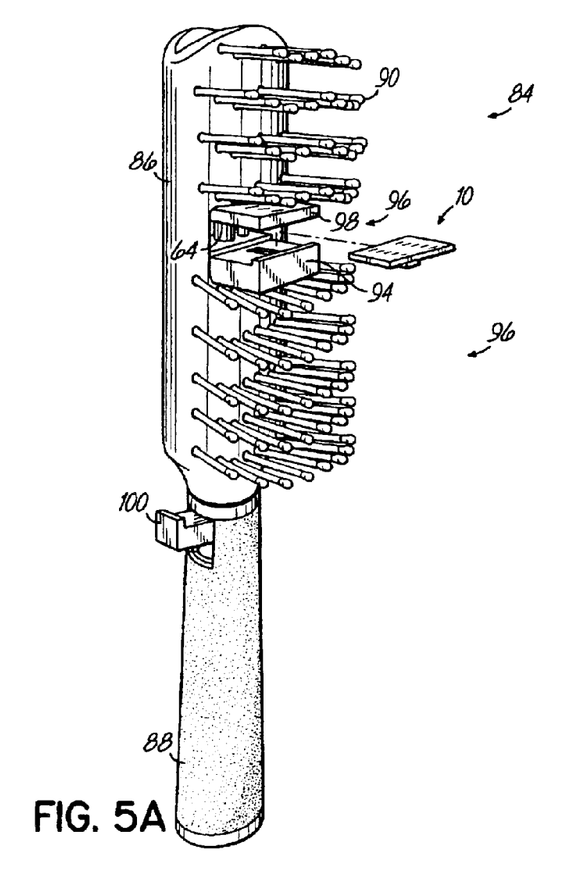
FIGS. 5A and 5B are side elevational views of a hair brush incorporating the directional coupler sensor of the present invention.
Figure 5B:
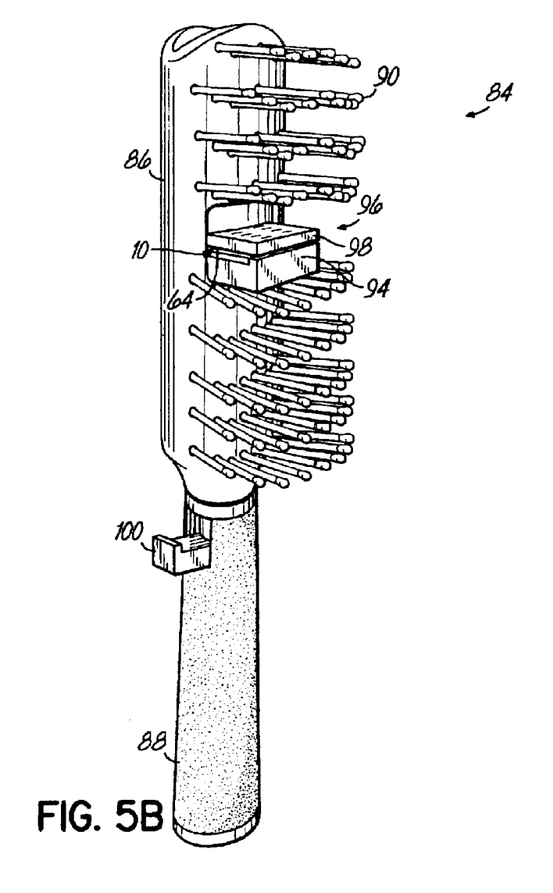

In accordance with another aspect of the present invention, as shown in FIGS. 5A and 5B, the sensor 10 is incorporated into a hair care product, such as a brush 84, used for grooming hair. The brush 84 includes an elongated body portion 86 terminating in a handle 88. Bristles 90 extend in a conventional manner from the body portion 86 of the brush 84 to enable grooming of the hair. In accordance with the principles of the present invention, as shown in FIG. 3, the signal generator 22, mixer 30, voltage regulator 92 (FIG. 2E) and electronics of the pressure sensor 62 are all integrated onto the PCB board 18 which is supported on a fixed base 94 of a hair clamping device 96 (FIGS. 5A and 5B). The fixed base 94 positions the directional coupler 12 near the bristles 90 so that measurements are easily taken while the hair is being brushed. The hair clamping device 96 includes a spring biased clamp member 98 that positions the pressure transducer 64 in juxtaposition to the directional coupler 12. A lever 100 is operatively connected to the movable clamp member 98 to enable a user to clamp hair across the coupling gap 16 when a sensor measurement is desired by moving the clamp member 98 toward the fixed base 94 as shown in FIG. 5B. The hair brush 84 may include LED's, and/or produce an audible signal, to provide an indication to the user about the moisture condition, health or other condition of the hair based on the sensor measurement. While not shown, in will be appreciated that the sensor 10 of the present invention may be incorporated into other hair care products as well, such as a comb, curling iron, or similar hair care product that preferably engages the user's hair during grooming to provide a measurement of the moisture content, health or other status of the hair based on the sensor measurement.

The directional coupler sensor 10 of the present invention is well suited to measure the moisture content, health or other condition of hair since it possesses sensitivity to variations in impedance in close proximity, such as about 0.1 in., to the surfaces of the strips 14a and 14b. The height of this effective measurement probing depth from the surfaces of the strips 14a, 14b is a function of the electromagnetic field that couples the strips 14a and 14b. The height of the measurement probing depth may be changed for a particular application by changing the height of the PCB 18, the dielectric constant of the PCB 18, the dimensions of the strips 14a, 14b, the coupling gap distance "s", and/or the power supplied by the signal generator 22. By varying any or all of these parameters, the height of the coupling field can be altered to thereby change the effective measurement probing depth.

It is contemplated that sensor 10 may comprise multiple directional couplers 12 electrically coupled to at least one signal generator 22 to measure the respective moisture content of multiple substrates in accordance with the principles described in detail above. It is further contemplated that at least two of the multiple directional couplers 12 may have different effective measurement probing depths by varying one or more of the parameters described in detail above.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor for measuring moisture content of a substrate having an impedance, said sensor comprising:
   a directional coupler having a pair of generally parallel first and second strips defining a coupling gap therebetween;
   a high frequency signal generator electrically coupled to said first strip and operable to couple power to said second strip with the substrate placed across said coupling gap to thereby generate a coupled power signal in said second strip having an amplitude related to the impedance, to thereby indicate the moisture content of the substrate; and
   a printed circuit board having a dielectric constant;
   wherein said first and second strips of said directional coupler are supported on said printed circuit board, and said high frequency signal generator is integrated onto said printed circuit board.

2. The sensor of claim 1 wherein said high frequency signal generator is operable to generate a forward power signal in said first strip and a reverse power signal in said second strip.

3. The sensor of claim 2 further comprising a mixer circuit electrically coupled to said first and second strips and operable to receive said forward power signal from said first strip and said reverse power signal from said second strip to thereby generate an output voltage signal having a value related to moisture content of the substrate.

4. The sensor of claim 1 wherein said high frequency generator operates in a range between about 30 MHz and about 3 GHz.

5. The sensor of claim 1 wherein a said high frequency generator is operable to generate an electromagnetic field that couples aid first and second strips of said directional coupler and defines an effective measurement probing depth relative to said first and second strips.

6. A sensor for measuring moisture content of a substrate, said sensor comprising:
   a directional coupler having a pair of generally parallel first and second strips defining a coupling gap therebetween; and
   a high frequency signal generator electrically coupled to said first strip and operable to couple power to said second strip with the substrate placed across said coupling gap to thereby generate a coupled power signal in said second a strip having an amplitude related to the moisture content of the substrate, said high frequency signal generator being operable to generate an electromagnetic field that couples said first and so strips of said directional coupler to define an effective measurement probing depth, said sensor having a printed circuit board with a dielectric constant, predetermined dimensions of said first and second strips, a coupling gap between said first and second strips, and a predetermined power supplied by said signal generator, wherein said measurement probing depth is variable and dependent upon a factor selected from the group consisting of said dielectric constant, said dimensions of said strips, said coupling gap, and the power supplied by said signal generator.

7. The sensor of claim 5 further comprising:
   a plurality of directional couplers each having a pair of generally parallel first and second strips defining a coupling gap therebetween; and
   a high frequency generator electrically coupled to said first strip of each said directional coupler and operable to couple power to said second strip of each said directional coupler with a substrate placed across said coupling gap of each said directional coupler to thereby generate a coupled power signal in each said respective second strip having an amplitude related to moisture content of each respective substrate.

8. The sensor of claim 7 wherein at least two of said plurality of directional couplers have different effective measurement probing depths.

* * * * *